United States Patent
Sander

(10) Patent No.: US 7,586,676 B2
(45) Date of Patent: Sep. 8, 2009

(54) OPTICAL DEVICE WITH INCREASED DEPTH OF FIELD

(75) Inventor: Ulrich Sander, Rebstein (CH)

(73) Assignee: Leica Microsystems (Schwiez) AG, Heerbrugg (CH)

( * ) Notice: Subject to any disclaimer, the term of this patent is extended or adjusted under 35 U.S.C. 154(b) by 0 days.

(21) Appl. No.: 11/754,420

(22) Filed: May 29, 2007

(65) Prior Publication Data

US 2007/0279733 A1    Dec. 6, 2007

(30) Foreign Application Priority Data

May 30, 2006  (DE) ................. 10 2006 025 149

(51) Int. Cl.
   *G02B 21/00*  (2006.01)
   *G02B 5/08*   (2006.01)
(52) U.S. Cl. .................... 359/383; 359/226; 359/368; 359/854
(58) Field of Classification Search ......... 359/224–227, 359/368–390, 846–861, 290–296
   See application file for complete search history.

(56) References Cited

U.S. PATENT DOCUMENTS

| | | | | |
|---|---|---|---|---|
| 5,299,053 | A * | 3/1994 | Kleinburg et al. ........... | 359/227 |
| 5,896,223 | A | 4/1999 | Tigliev et al. | |
| 6,399,935 | B1 * | 6/2002 | Jovin et al. .................. | 250/216 |
| 6,483,641 | B1 * | 11/2002 | MacAulay ................... | 359/385 |
| 7,002,739 | B2 * | 2/2006 | Awamura .................... | 359/385 |
| 7,068,416 | B2 | 6/2006 | Gim et al. | |
| 7,206,127 | B2 | 4/2007 | Sander | |
| 7,215,882 | B2 | 5/2007 | Cho et al. | |
| 2003/0063376 | A1 * | 4/2003 | Shimizu et al. ............. | 359/380 |
| 2004/0017607 | A1 * | 1/2004 | Hauger et al. ............... | 359/376 |
| 2006/0171263 | A1 * | 8/2006 | Cho et al. ................. | 369/44.23 |
| 2009/0040586 | A1 * | 2/2009 | Kim et al. ................... | 359/223 |

* cited by examiner

*Primary Examiner*—Thong Nguyen
(74) *Attorney, Agent, or Firm*—Hodgson Russ LLP

(57) ABSTRACT

An optical device for imaging a specimen (16) has a main objective (2) and a device (120) for modifying depth of field, the device (120) representing a micromirror array (5') having micromirrors (50) that are individually controllable and adjustable as to their spatial orientation. In addition to the increase in depth of field, a variable objective can also be produced. The invention is particularly suitable for use in a microscope where deflection of the observation beam path is present.

10 Claims, 4 Drawing Sheets

OPTICAL DEVICE WITH INCREASED DEPTH OF FIELD

CROSS REFERENCE TO RELATED APPLICATIONS

This application claims priority of German patent application no. 10 2006 025 149.0 filed May 30, 2006 which is incorporated by reference herein.

FIELD OF THE INVENTION

The invention relates to an optical device, in particular to a stereomicroscope, for imaging a specimen, having a main objective and a device for modifying depth of field or the effective focal length of the main objective of the optical device.

BACKGROUND OF THE INVENTION

Microscopes comprise at least two imaging optical elements, namely a main objective and an eyepiece. All optical observation devices possess, in principle, the same fundamental construction. The two optical elements (objective and eyepiece) form an overall system that defines the potential magnification range as well as the depth of field. In most optical devices the depth of field, i.e. the region in which one or more specimen points located on the optical axis are imaged in focus at the same time, is very limited. An increase in depth of field is desirable in order to present a more comprehensive image to the observer. In many microscope application areas, in particular those for surgical microscopes (e.g. for neurosurgery), a particularly high degree of depth of field is important because the surgeon must view, sharply, not only the plane of focus but also as many specimen regions as possible in front of and behind the plane of focus.

In order to increase depth of field, it is known to increase the focal length of the lens system of the optical device and/or to make the aperture smaller. In the field of application of microscopes, the former possibility is almost excluded since the focal length range is limited. Because the depth of field decreases with increasing microscope magnification, only a thin object plane can be imaged sharply. The second possibility for increasing depth of field, by making the aperture smaller, results in a decrease in image brightness and a loss of resolution and contrast.

An optical device according to the present invention for imaging a specimen is equipped with a main objective and a device for modifying depth of field, the device for modifying depth of field comprising a micromirror array having micromirrors that are individually controllable and adjustable as to their spatial orientation.

Micromirror arrays as such are known from the existing art. They are generally made up of a two-dimensional arrangement of individual mirrors whose positions are adjustable individually or in suitable combination. The micromirrors are joined to a stationary support element. By appropriate adjustment of the micromirrors while the support element remains stationary, it is possible to implement a beam deflection system that consequently requires little space. The absence of a need for pivoting of a support element or deflection element thus contributes to a small overall height for the optical device (microscope), and permits highly accurate alignment and almost vibration-free operation.

Because the micromirrors can assume various angular positions relative to one another, two or more different deflection angles can be implemented simultaneously with one micromirror array. The adjustability of the micromirrors makes possible, in particular, a flexible selection of the deflection angle. For example, the spatial orientation of the micromirrors (and therefore the deflection angle) can be modified as a function of time. On the other hand, it is possible to implement (statically) two or more deflection angles by corresponding orientation of the micromirrors on the micromirror array, so that beam paths arriving from one direction are diverted in different directions or, as utilized for the present invention, beam paths arriving from different directions are diverted in the same direction.

It is thus possible in this fashion for specimen points that are located outside the focal plane and can no longer be imaged (or can no longer be imaged sharply) by the optical device to be imaged by the optical device in a context of appropriate adjustment of the micromirrors.

In an advantageous embodiment of the invention, at least a portion of the micromirrors of the micromirror array are consequently adjustable in such a way that an observation ray bundle or beam path of a specimen point located outside the focal plane is imaged, as a result of a substantially spherical spatial orientation of the relevant micromirrors, in the same fashion as a specimen point located in the focal plane in the context of micromirrors oriented substantially parallel to one another.

It is additionally advantageous if the micromirrors of the micromirror array are adjustable in such a way that multiple specimen points located along the optical axis proceeding through the main objective are each imaged in the same fashion, simultaneously or in chronological sequence, by means of differing static orientations of the micromirrors or by means of an orientation of the micromirrors that changes over time. As already discussed, different deflection angles (and therefore orientations) of the relevant micromirrors can be implemented in a micromirror array both simultaneously and in chronological sequence. By suitable orientation of the relevant micromirrors, two or more specimen points located in the direction of the optical axis can thus simultaneously be effectively imaged into infinity by means of the main objective and the micromirror array, and thus sharply imaged by the optical device, with the result that depth of field is increased.

On the other hand, in the context of a chronologically sequential change in the orientation of the relevant micromirrors, an entire range of specimen points located along the optical axis can also be effectively imaged into infinity by means of the main objective and the micromirror array, with the result that depth of field is increased in the same fashion.

In the former case of simultaneous imaging of different specimen points on the optical axis, it is useful to place these specimen points so that the depth-of-field regions associated with them (present in system-inherent fashion as manufactured) end up located adjacently to one another. A large depth of field can thus be attained by summation of depth-of-field ranges.

In the case of chronologically sequential imaging of a range of specimen points located on the optical axis, it is useful to run through this range, by corresponding modifications of the micromirror orientations, so quickly that the observer (human eye or camera) has the impression of a static image. This is the case when the runthrough frequency is greater than or equal to the respective so-called flicker fusion frequency.

It must be noted, in the context of the optical device according to the present invention, that the end result of the device for modifying the depth of field is to modify the effective focal length of the main objective. This resulting variation in the effective focal length of the main objective (the invention thus implements a variable objective) causes, in the context of a microscope, a change in the microscope magnification and therefore a pulsing of the image and a distortion of the stereoscopic impression. The range of specimen points to be imaged should consequently be selected correspondingly so that these negative effects are not too greatly evident. Furthermore, in an advantageous embodiment, an attempt can be made to counteract these effects by largely compensating for the resulting changes in microscope magnification by way of an opposite-direction change in the zoom magnification of a downstream zoom system. Rapid application of control to the zoom system, with short reaction times, is necessary for this purpose.

As has already been noted repeatedly, it is advantageous if the optical device is a microscope, in particular a stereomicroscope, in particular a surgical microscope.

The device according to the present invention, configured as a micromirror array, for modifying depth of field also allows implementation of a variable objective, as already discussed. By way of a corresponding spherical orientation of the micromirrors of the micromirror array, the focal length of the main objective can be effectively modified with no need to effect changes to the main objective itself.

The rapid, delay-free, low-vibration adjustability of the micromirrors of a micromirror array makes possible in user-friendly fashion, especially in the context of high-precision devices such as surgical microscopes, specimen examination with increased depth of field or with a modifiable main objective focal length.

BRIEF DESCRIPTION OF THE DRAWINGS

The invention will be further explained below with reference to an exemplifying embodiment illustrated in the drawings.

The illustration of the invention using the example of a microscope is not of a limiting nature. The features of the invention that are depicted can be implemented not only in the combination set forth here, but also in other combinations or in isolation.

In the drawings:

Figure 1:
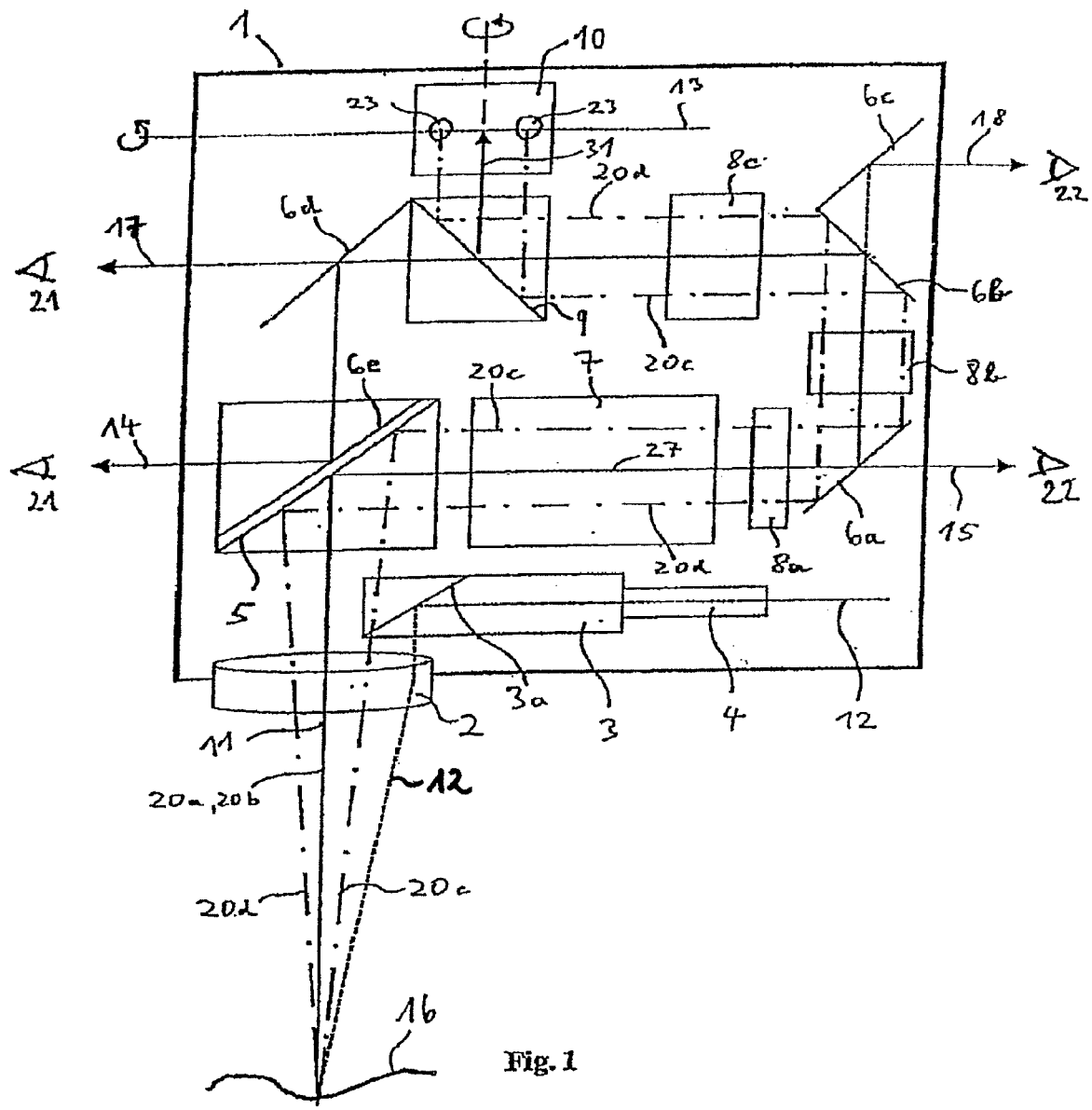
Figure 2:
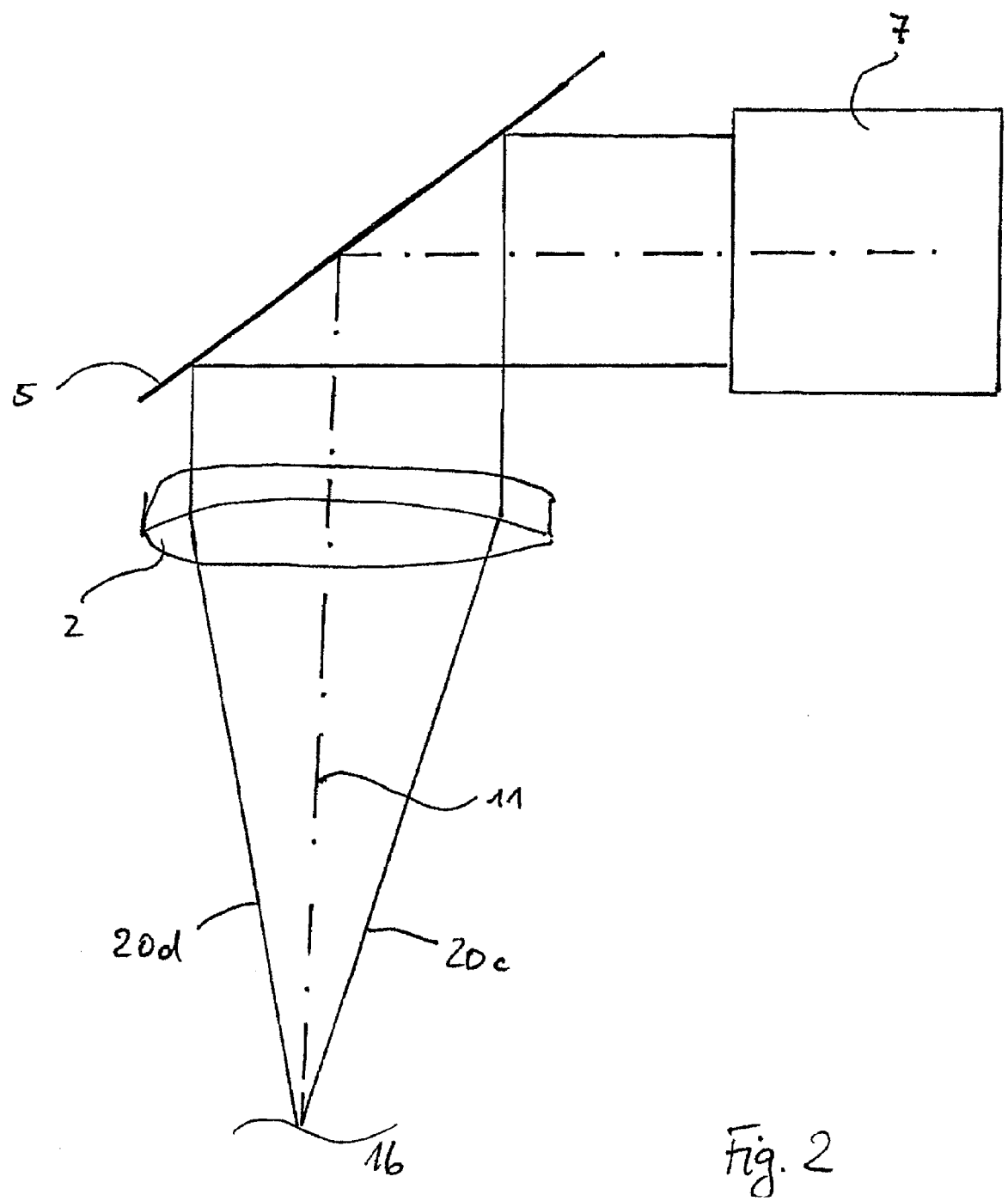
Figure 3:
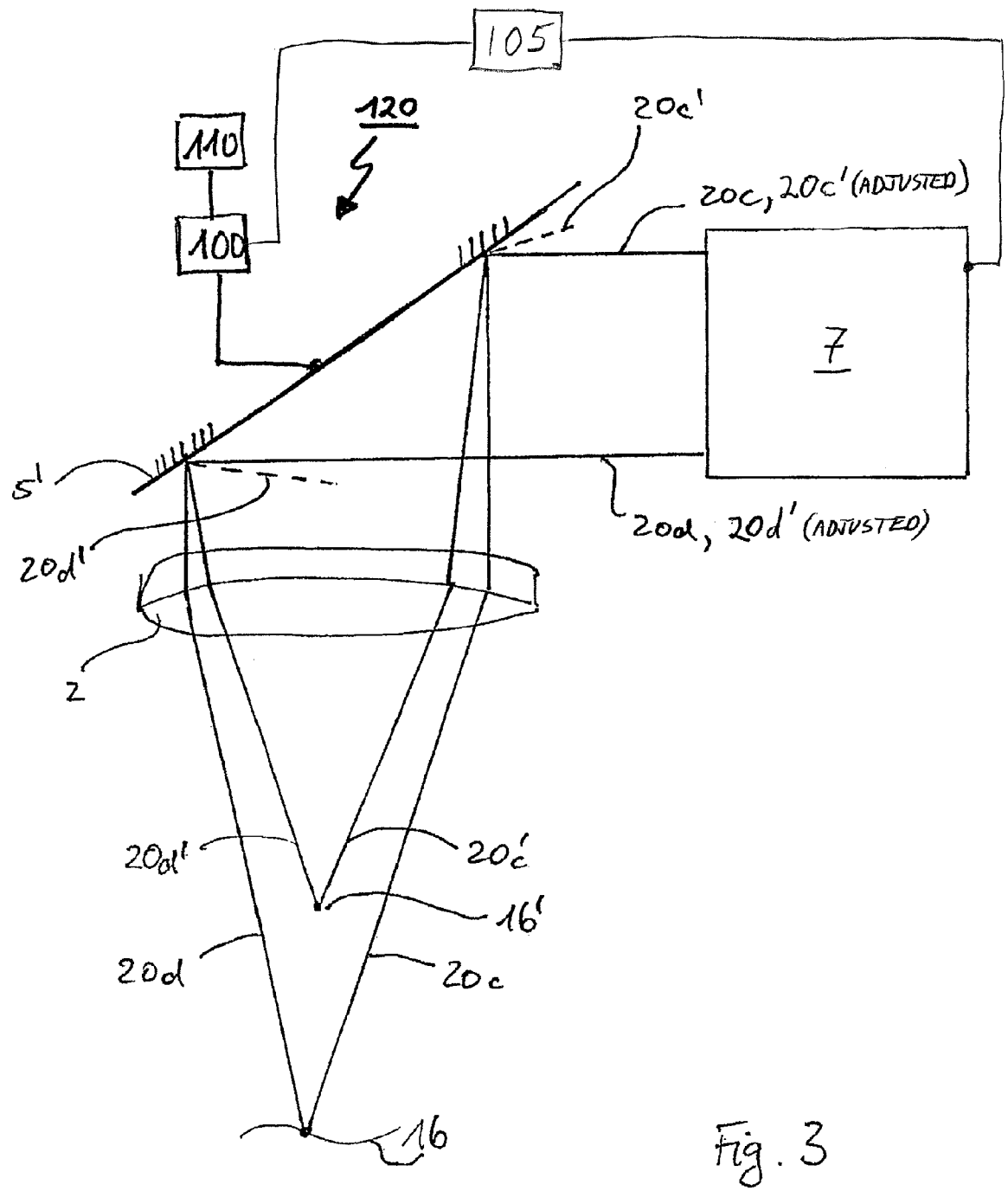
Figure 4A:
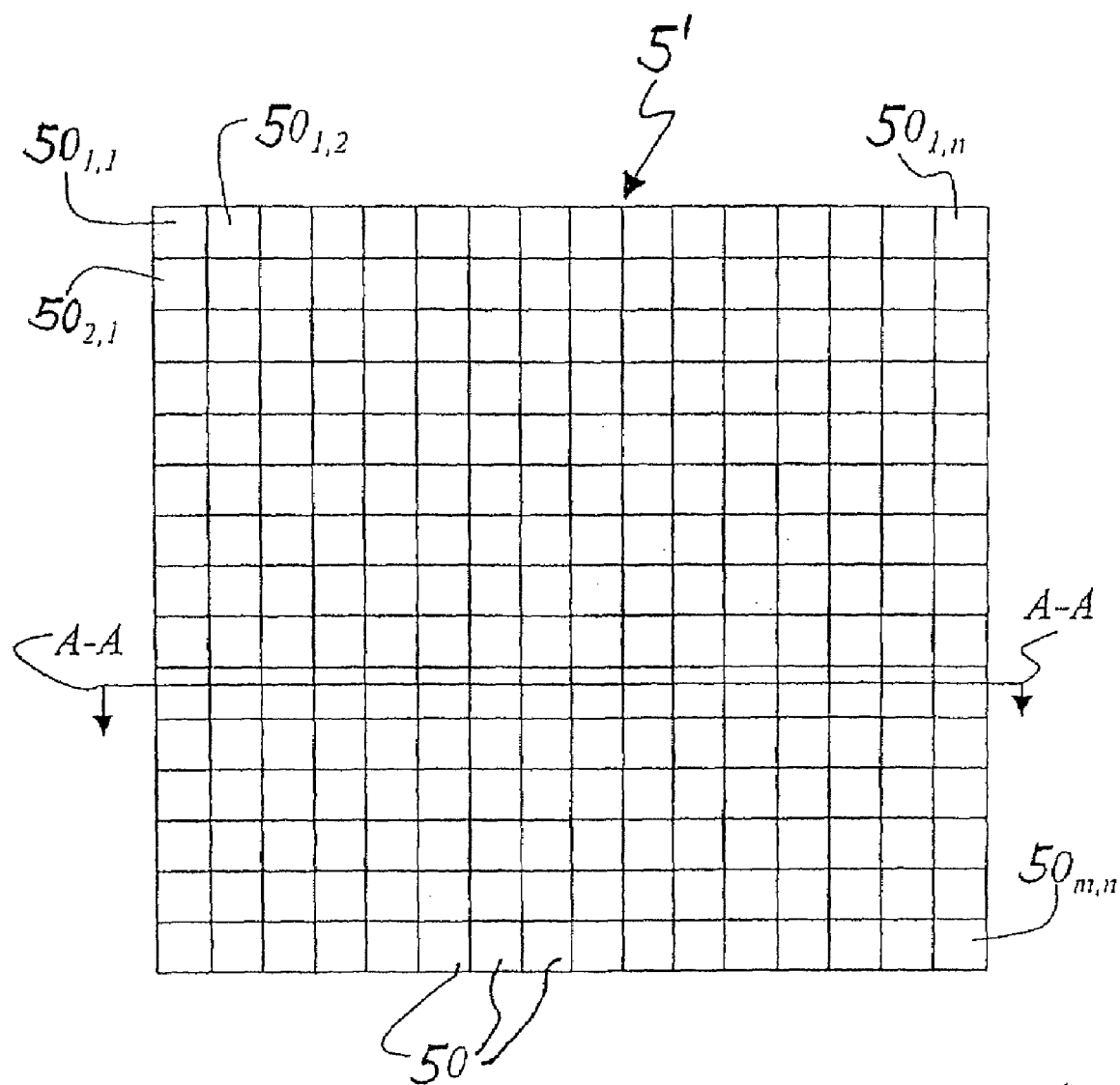

FIG. 1 schematically depicts a microscope configuration known from the existing art;

FIG. 2 is a detail view of elements of the microscope of FIG. 1;

FIG. 3 is the detail view of FIG. 2 with a device according to the present invention for modifying depth of field or the effective focal length of the main objective;

FIG. 4A is a schematic plan view of a micromirror array; and

Figure 4B:
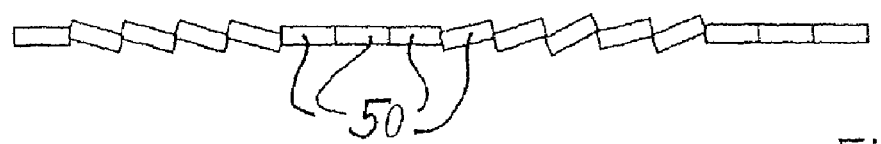

FIG. 4B is a schematic sectional view of a micromirror array taken along line A-A in FIG. 4A.

DETAILED DESCRIPTION OF THE INVENTION

FIG. 1 shows an embodiment of a stereomicroscope according to DE 102 55 960 A1 (corresponding to U.S. Pat. No. 7,206,127) that will be explained briefly below. A schematically depicted microscope body of a stereomicroscope is labeled 1 in its entirety. The stereoscopic axes are located behind one another as depicted in FIG. 1, so that only one axis is visible. The stereomicroscope depicted is, in particular, an opthalmologic microscope with which a specimen 16 is to be observed and examined. The stereomicroscope comprises, as essential optical components, a main objective 2, a zoom system 7, and an eyepiece system (not depicted).

A first deflection element 5 is provided between main objective 2 and zoom system 7. Provided behind zoom system 7 are further deflection elements 6a, 6b, 6c, 6d, 6e, 9, and 10, as well as additional optical components 8a to 8c whose function will be explained later on.

The number 3 designates an illumination unit that directs light, made available by means of a fiber-optic cable 4, via a deflection element 3a onto specimen 16 to be observed. The main axis of illumination device 3 is labeled 12. In the case depicted, the illumination beam path runs through main objective 2. Also conceivable, however, is an arrangement in which the illumination is guided past main objective 2.

Zoom system 7 of the stereomicroscope usually comprises two main observation channels and, in the present case, additionally two assistant's observation channels.

Passing through main objective 2 in a substantially vertical direction are two main observation ray bundles 20a, 20b (lying behind one another in the drawing) and two assistant's observation ray bundles 20c, 20d that, after a corresponding (right-angle) deflection by deflection element 5, enter the substantially horizontally extending main and assistant's observation channels of zoom system 7. After their emergence from zoom system 7, a further deflection of observation ray bundles 20a to 20d occurs at further deflection element 6a.

By means of this deflection element 6a, observation ray bundles 20a to 20d are deflected substantially back into the vertical, whereupon they strike a further deflection element 6b by means of which another deflection occurs into the horizontal, whereupon a deflection once again occurs at deflection element 9. Be it noted at this juncture that deflection elements 6a and/or 6b can be embodied as optical beam splitters with which the observation axes (labeled 15 and 18, respectively) for assistant observers 22 can be defined. A further deflection element 6c is used here to generate observation axis 18. This kind of configuration of an assistant's observation system is entirely optional.

The binocular tubes and eyepieces necessary, for observation, for the main observer 21 and assistant observer 22 are not shown in FIG. 1 for the sake of clarity.

Deflection element 9 is embodied in such a way that it deflects only ray bundles 20c, 20d, while ray bundles 20a, 20b pass through deflection element 9 without deflection and strike further deflection element 6d. The use of a deflection element of this kind makes possible, in simple fashion, a physical separation of main observation ray bundles 20a, 20b from assistant's observation ray bundles 20c, 20d with no loss in light intensity. Main observation ray bundles 20a, 20b define observation axis 17 and, after further deflection at deflection elements 6e, observation axis 14.

Optical components 8a, 8b, and 8c are additional components that can be inserted selectably, such as filters, laser shutters, optical splitters, data overlay systems, stops, displays, and the like.

The presentation of the configuration of microscope body 1, depicted in FIG. 1, of a stereomicroscope is merely exemplifying. The elements that are substantially of importance for the present invention are main objective 2, deflection mirror 5, and zoom system 7.

With regard to further embodiments and to the function and coaction of the components depicted in FIG. 1, the reader is otherwise referred explicitly to the aforesaid U.S. Pat. No. 7,206,127, the entirety of which is incorporated herein by reference.

The elements that are essential to an understanding of the invention, using the present example of an optical device according to FIG. 1 embodied as a stereomicroscope, are depicted again in detail in FIG. 2. Here 16 once again designates the specimen, 11 the axis of symmetry of the main objective or the optical axis proceeding through the main objective, 2 the main objective, 5 the deflection element arranged behind main objective 2, and 7 the zoom system. The numbers 20d and 20c are intended here to identify two observation ray bundles that are used for stereoscopic observation of specimen 16. These observation ray bundles represent assistant's observation ray bundles in FIG. 1, but the present FIG. 2 refers in general to observation ray bundles as such. Observation ray bundles 20d and 20c depicted in FIG. 2 are, however, particularly suitable for illustration of the invention because they both lie in the drawing plane. One skilled in the art can also transfer the present invention to the instance in which such observation ray bundles are arranged in a plane perpendicular to the drawing plane, or in another plane.

As is evident from FIG. 2, observation ray bundles 20d and 20c are imaged into infinity by means of main objective 2 and are then deflected by deflection element 5, substantially perpendicular to axis 11, into zoom system 7. Other specimen points located on axis 11 that are located outside the focal plane of main objective 2 extending through specimen 16 are not imaged into infinity by the main objective and cannot, after deflection by deflection element 5, enter the stereoscopic channels of zoom system 7. The reader is referred, for this, to the depiction in FIG. 3.

As depicted in FIG. 3, observation ray bundles 20d' and 20c' proceeding from specimen point 16' extend behind main objective 2 of the stereomicroscope not in parallel but in divergent fashion, as is apparent from lines 20d' and 20c' (drawn as dashed lines), after deflection at deflection element 5'. These divergent beams can thus not reach the channels of zoom system 7 or pass through them, so that imaging of specimen point 16' cannot take place.

Be it noted at this juncture that the optical system depicted in FIG. 3 (like other optical devices as well) has a depth of field that depends on the optical components of the system. As already presented initially, this depth of field can be influenced by modifying focal length and/or aperture. For the explanations that follow it will be assumed, with no limitation as to generality, that specimen point 16' is located outside the depth-of-field range inherent in the system depicted.

If, as depicted in FIG. 3, an object plane 16' is also to be imaged sharply, the optical refractive power of system 2, 7 must be modified in such a way that, as depicted, beams 20d' and 20c' travel into zoom system 7 in the same way as beams 20d, 20c. The refractive power of the system is modified for this purpose. This is done, according to the present invention, by a device 120 for modifying depth of field and/or for changing the effective focal length of main objective 2. This device 120 according to the present invention represents substantially a micromirror array 5' having micromirrors 50 that can be individually controlled and adjusted as to their spatial orientation (cf. FIG. 4). This micromirror array 5' is powered by a control unit 100 and an operating unit 110, which are depicted merely schematically. Details of the application of control to a micromirror array are known from the existing art and will therefore not be reproduced in detail below. By means of control unit 100, the individual micromirrors 50 of micromirror array 5' can be adjusted, individually or in suitable combination with one another, as to their spatial orientation. The reflection direction of each individual micromirror 50 can thus be adjusted. A micromirror array 5' is depicted schematically in FIG. 4.

The overall result of the micromirror array is to cause a deflection of the observation beam path guided through the main objective of the optical device. This deflection can be utilized, as explained in more detail below, to reduce the overall height of the optical device.

It is useful in this context if the micromirror array is arranged behind the main objective of the optical device when viewed from the specimen, the specimen to be imaged being arranged, as usual, in the focal plane of the main objective. The micromirror array thus acts as a deflection element for the parallel observation beam path coming from the main objective. This beam path can, farther along, be conveyed to optical elements. These optical elements can be data overlay systems, shutters, filters, transparent displays, beam deflection systems, or image erectors, as well as intermediate imaging and/or magnification systems. With no limitation as to generality, the basis for illustration of the present invention, unless otherwise indicated, will be an (afocal) zoom system downstream from the micromirror array and permitting stepless magnification. Such zoom systems are usually used in microscopes, in particular stereomicroscopes such as surgical microscopes.

In the context of this kind of configuration, discussed by way of example, of an optical device (microscope) that has a main objective, a micromirror array acting as a deflection element for the observation beam path, and a downstream zoom system, depth of field is modified or increased as follows: The micromirror array is usefully arranged to perform a 90-degree deflection, toward the zoom system, of the parallel observation beam path coming from the main objective. For this purpose, the micromirrors of the micromirror array can be set in planar fashion if the support element is arranged at an angle of 45° with respect to the observation beam path. With a different (less preferred) arrangement of the support element, the micromirrors would be arranged substantially parallel to one another. With the preferred former support element arrangement, all the micromirrors consequently lie in the same plane. When a specimen point outside the plane of focus—e.g. between the object plane (focal plane) and main objective—is then viewed, the beam path proceeding from this specimen point is not imaged into infinity by the main objective, so that after deflection of the beam path at the micromirror array in a context of a planar arrangement of the micromirrors, the beam path does not reach the zoom system and is thus not available for further imaging. In the presently considered case of a specimen point located between the focal plane and main objective, that point's observation beam path would be deflected divergently and would bypass the zoom system. The use according to the present invention of a micromirror array now makes it possible, by suitable orientation of micromirrors, to reflect at least a portion of this observation beam path into the zoom system by tilting the relevant micromirrors out of their planar orientation into a physically spherical orientation, with the result that after deflection at the micromirror array, the divergent ray bundle proceeds in parallel fashion. Two (or more) specimen points located along the optical axis can in this fashion be sharply imaged, like a specimen point that is in focus.

In the subregions of the micromirror array 5' that are designated with crosshatching in FIG. 3, a modified reflection of beams 20d' and 20c' can be achieved by corresponding spatial orientation of the relevant micromirrors, in such a way that said beams, like beams 20c and 20d, are directed into zoom system 7. What is necessary overall for this is a corresponding spherical physical orientation, in the manner of a concave mirror, of the relevant micromirrors in the subregions of micromirror array 5' designated with crosshatching. If the relevant micromirrors in the crosshatched regions are given the spherical orientation necessary for this purpose, specimen point 16' is imaged sharply by the system, but imaging of specimen 16 would no longer be possible. In this case device 120 according to the present invention would have the function of modifying the effective focal length of main objective 2, i.e. would be suitable for implementing a variable objective (using a main objective 2 of fixed focal length!).

If, on the other hand, the depth of field of the system is to be increased in such a way that specimens 16 and 16' are sharply imaged by the optical device (partially) depicted in FIG. 3, the aforesaid operation of modifying the orientation of the micromirrors in the crosshatched subregions of micromirror array 5' must be performed either simultaneously or in (as rapid as possible) chronological sequence.

With reference to the first alternative, within the crosshatched subregions of micromirror array 5' one portion of the micromirrors can remain aligned in planar fashion (cf. FIG. 2) and another portion of the micromirrors can, as mentioned, assume the aforesaid spherical orientation, so that points 16 and 16' are simultaneously sharply imaged and the associated observation ray bundles 20d, 20c and 20d', 20c' all enter zoom system 7. Micromirror array 5' would then have, at least in the crosshatched subregions, planar (i.e. purely reflective) components as well as spherically modified regions. These regions can be located next to one another or can overlap.

To allow sharp imaging, with the aforesaid system, of specimen points located between specimen points 16 and 16' that are depicted, it would be conceivable additionally to introduce further spherical orientations into the crosshatched subregions of micromirror array 5'. Another possibility is to modify the orientations of the micromirrors over time in such a way that, starting from the planar arrangement (for imaging specimen point 16), they run through the corresponding spherical orientations up to that spherical orientation which is necessary for imaging specimen point 16'. The specimen points located between specimen points 16 and 16' are thereby sharply imaged. This procedure can be configured cyclically. If the frequency of this cycle is greater than or equal to the flicker fusion frequency, the chronological sequence is no longer noticed, but the image is instead perceived as static. The flicker fusion frequency for the human eye is defined, and depends substantially on the ambient brightness. Corresponding flicker fusion frequencies can also be defined in analogous fashion for downstream image detectors such as cameras.

With this advantageous configuration, the entire specimen-point range between 16 and 16' can be sharply imaged, and depth of field can thus be drastically increased as compared with conventional optical devices. What results for the observer is a static image corresponding to a large depth of field. Because only very small micromirrors need to be modified as to their spatial orientation, it is possible to work in almost vibration-free fashion. Very rapid application of control to these micromirrors is also possible by way of control unit 100. The optically relevant space requirement of the device according to the present invention is furthermore limited to the volume of micromirror array 5'. Additional optical components, or parts requiring mechanical displacement, are not necessary.

According to the present invention, the effective focal length of main objective 2 is changed by the change in the refractive power of the system, even though a main objective 2 of fixed focal length can be used. Associated with this is a changing overall magnification of the microscope. The range between specimen points 16 and 16' is therefore, in practice, dimensioned in such a way that the difference in magnification corresponding to the change in focal length does not produce an unpleasant visual impression, i.e. does not bring about a distortion of the stereoscopic impression or pulsing of the image.

In a further particularly advantageous embodiment of the invention, the aforesaid fluctuation of the microscope magnification that is produced, and thus a distortion of the stereoscopic impression or pulsing of the image, can also be actively counteracted by applying control to zoom system 7 through zoom control unit 105 in such a way that the latter generates an opposite-direction modification of the zoom magnification, so that altogether, the two effects are substantially compensated for. An increase in microscope magnification is thus compensated for by a decreased zoom magnification, and conversely a decreasing microscope magnification is compensated for by an increasing zoom magnification. In this case the range between specimen points 16 and 16' can once again be magnified.

Reference is made to FIG. 4 regarding the configuration of a micromirror array 5'. FIG. 4A shows a micromirror array 5' of this kind in a plan view, with a plurality of micromirrors 50 arranged in a matrix. Micromirrors $50_{1,1}, 50_{1,2} \ldots, 50_{1,n}$ are arranged in the first row. Micromirrors $50_{2,1} \ldots, 50_{2,n}$ are arranged in the second row, and so forth until micromirrors $50_{m,1}, 50_{m,2} \ldots, 50_{m,n}$ are arranged in the last row. Each of these micromirrors 50 can be controlled and adjusted as to its spatial direction, individually or in suitable combination with other micromirrors 50. FIG. 4B shows a section along line A-A of FIG. 4A. FIG. 4B illustrates the spatial orientation of micromirrors 50, an overall substantially spherical spatial alignment of micromirrors 50 being depicted here. The procedure for applying control to micromirrors 50 of a micromirror array 5' will not be explained in greater detail at present, since micromirror arrays are known in principle from the existing art.

The present invention is suitable for increasing the depth of field of an optical device with no need to modify imaging properties of the essential components. The invention requires no actuating motors or linkages, or their control application systems. All that is needed is a micromirror array, which can often replace deflection elements that are already present (cf. deflection element 5 in FIG. 1). In addition to the increase in depth of field, a variable objective can also be produced.

PARTS LIST

1 Microscope body
2 Main objective
3 Illumination unit
3a Deflection element
4 Fiber-optic cable
5 Deflection element
5' Micromirror array
6a, 6b, 6c, 6d, 6e Deflection elements
7 Zoom system
8a, b, c Additional optical components
9 Deflection element for assistant's beam path
10 Deflection element for pivoting the assistant's beam path
11 Axis of symmetry of main objective, optical axis
12 Axis of illumination device
13 Rotation axis of deflection element 10
14 Observation axis
15 Observation axis
16 Specimen
17 Observation axis
18 Observation axis
20a, 20b Main observation bundle
20c, 20d (Assistant's) observation bundle
21 Main observer
22 Assistant observer
23 Assistant's observation axis 27 Center axis of zoom system
31 Axis
50 Micromirrors
100 Control unit
110 Operating unit
120 Device for modifying depth of field Although the illumination intensity can be raised in order to increase the image brightness, this usually results in an increased thermal load on the specimen being examined, which can have a disadvantageous effect especially in the field of application of surgical microscopes (examination of living tissue).

Known stereomicroscopes of the Applicant such as, for example, the LEICA M651 and LEICA M690 models provide, in order to increase depth of field, a double iris diaphragm for simultaneously making the apertures of both stereoscopic beam paths smaller. This results, however, in the disadvantages already recited.

A further increase in depth of field (albeit technically very complex) is known from EP 0 988 572 B1 (corresponding to U.S. Pat. No. 5,896,223). What is provided here is a device that modifies the focal length of the system at very high speed. For this, either a lens is displaced along the beam path or a lens having different optical properties is introduced transversely into the beam path. Synchronously with this motion, a shutter opens the beam path only when the motion has arrived at its outermost point. The speed of this motion must be sufficiently high that so-called "stereoscopic pumping" or "pulsing" (image motion), and furthermore brightness flickering, do not occur. Leaving aside the aforementioned very high level of technical complexity, on a microscope such as a surgical microscope this approach is not practical simply for weight and space reasons. The large masses that need to be moved quickly furthermore impede high-precision alignment for image generation in a surgical microscope.

SUMMARY OF THE INVENTION

It is therefore an object of the present invention to provide, in the context of the aforesaid optical devices, a device with which depth of field can be varied, in particular increased, or in more general terms the effective focal length of the main objective of the optical device can be varied, without having to accept the disadvantages of the known existing art.

This object is achieved, according to the present invention, by an optical device as described herein. Advantageous embodiments of the invention are evident from the description below.

What is claimed is:

1. An optical device for imaging a specimen, the optical device comprising:
   a main objective having a focal plane intended to intersect a specimen and an optical axis; and
   a device for modifying a depth of field, wherein the device for modifying the depth of field includes a micromirror array having micromirrors that are individually controllable and adjustable as to their spatial orientation,
   wherein at least a portion of the micromirrors of the micromirror array are adjusted in a substantially spherical spatial orientation such that an observation ray bundle of a specimen point located on the optical axis outside the focal plane of the main objective is imaged substantially as sharply as an observation ray bundle of a specimen point located on the optical axis in the focal plane of the main objective.

2. The optical device according to claim 1, wherein the micromirror array is arranged after the main objective along an observation beam path coming from a specimen.

3. The optical device according to claim 1, wherein the micromirrors of the micromirror array are adjusted in such a way that at least two different specimen points located along the optical axis of the main objective are simultaneously sharply imaged.

4. The optical device according to claim 1, wherein the micromirrors of the micromirror array are adjusted in such a way that at least two different specimen points located along the optical axis of the main objective are sharply imaged in chronological sequence.

5. The optical device according to claim 4, wherein the micromirrors of the micromirror array are adjusted periodically at a frequency that is greater than or equal to a flicker fusion frequency of an observer using the optical device.

6. The optical device according to claim 1, wherein the optical device is a microscope further comprising a zoom system arranged after the micromirror array along an observation beam path coming from a specimen.

7. The optical device according to claim 6, wherein the microscope is a stereomicroscope.

8. A microscope for imaging a specimen, the microscope comprising:
   a main objective having a focal plane intended to intersect a specimen and an optical axis;
   a device for modifying a depth of field, wherein the device for modifying the depth of field includes a micromirror array having micromirrors that are individually controllable and adjustable as to their spatial orientation, wherein at least a portion of the micromirrors of the micromirror array are adjusted in a substantially spherical spatial orientation such that an observation ray bundle of a specimen point located on the optical axis outside the focal plane of the main objective is imaged substantially as sharply as an observation ray bundle of a specimen point located on the optical axis in the focal plane of the main objective; and
   a zoom system arranged after the micromirror array along an observation beam path coming from the specimen, wherein the zoom system is adjusted to provide a magnification that counteracts change in microscope magnification caused by adjustment of the micromirrors of the micromirror array.

9. A method of modifying a depth of field of an optical device for imaging a specimen, the optical device having a focal plane intersecting the specimen and an optical axis intersecting the focal plane, the method comprising the steps of:
   providing a micromirror array in an observation beam path of the optical device, the micromirror array having a plurality of micromirrors individually controllable and adjustable as to their spatial orientation; and
   adjusting at least a portion of the plurality of micromirrors to a substantially spherical spatial orientation such that an observation ray bundle of a specimen point located on the optical axis outside the focal plane of the optical device is imaged substantially as sharply as an observation ray bundle of a specimen point located on the optical axis in the focal plane of the optical device.

10. The method according to claim 9, further comprising the step of adjusting a zoom system of the optical device to provide a magnification that counteracts change in magnification caused by adjustment of the micromirrors of the micromirror array.

* * * * *